United States Patent [19]

Mihara et al.

[11] Patent Number: 4,677,053
[45] Date of Patent: Jun. 30, 1987

[54] SILVER HALIDE PHOTOGRAPHIC MATERIALS

[75] Inventors: Yuji Mihara; Toshinao Ukai, both of Kanagawa, Japan

[73] Assignee: Yuji Mihara, Japan

[21] Appl. No.: 600,635

[22] Filed: Apr. 16, 1984

[30] Foreign Application Priority Data

Apr. 15, 1983 [JP] Japan .................................. 58-66631

[51] Int. Cl.⁴ .................. G03C 1/20; G03C 1/28; G03C 1/08
[52] U.S. Cl. .................... 430/576; 430/600; 430/584
[58] Field of Search ............... 430/576, 584, 614, 573, 430/600

[56] References Cited

U.S. PATENT DOCUMENTS

| | | | |
|---|---|---|---|
| 2,131,038 | 9/1938 | Brooker et al. | 430/614 |
| 3,556,800 | 1/1971 | Kimura et al. | 430/584 |
| 3,615,641 | 10/1971 | Shiba et al. | 430/576 |
| 3,635,721 | 1/1972 | Sato et al. | 430/576 |
| 3,706,567 | 12/1972 | Hiller | 430/576 |
| 3,809,561 | 5/1974 | Ulbing et al. | 430/576 |
| 4,138,266 | 2/1979 | Hinata et al. | 430/576 |

Primary Examiner—Won H. Louie
Attorney, Agent, or Firm—Sughrue, Mion, Zinn, Macpeak, and Seas

[57] ABSTRACT

A silver halide photographic material comprising a support having thereon at least one silver halide photographic emulsion containing at least one infrared sensitizing dye represented by following general formula (I)

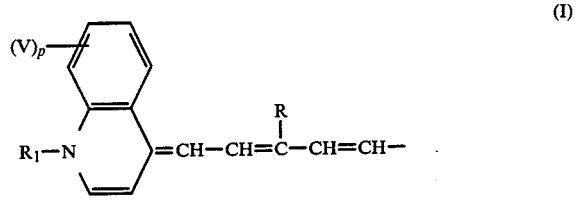

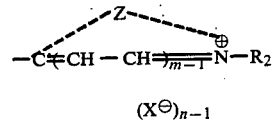

and at least one compound represented by following general formula (II)

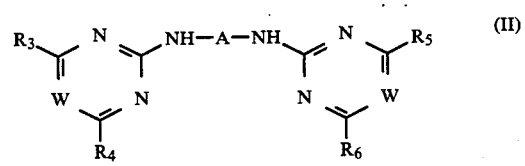

wherein R, $R_1$, $R_2$, V, Z, X, m, n, p, A, $R_3$, $R_4$, $R_5$, $R_6$ and W are defined in the specification.

8 Claims, No Drawings

SILVER HALIDE PHOTOGRAPHIC MATERIALS

FIELD OF THE INVENTION

This invention relates to a silver halide photographic material spectrally sensitized to an infrared-sensitive region, and more particularly to a silver halide photographic material having improved sensitivity in an infrared spectral region and improved shelf life.

BACKGROUND OF THE INVENTION

One image-forming process using silver halide photographic materials is an image-forming process using the so-called scanner system, i.e., a process of scanning an original and exposing a silver halide photographic material in conformity with the image signal to form a negative image or a positive image corresponding to the original image. Various recording devices for the image-forming process using the scanner system are known and a glow lamp, a xenon lamp, a mercury lamp, a tungsten lamp, a luminous diode, etc., have been used as a recording light source for these recording devices. However, these light sources have the practical disadvantage that the output is weak and a short life. A scanner using a coherent laser light source such as Ne-Ne laser, argon laser, He-Cd laser, etc., as the light source for the scanner system is a system for overcoming these difficulties. However, such a system has also the disadvantages that the apparatus is large and expensive, a modulator is required, and further a safe light for a photographic material is restricted since visible light is used. This makes the handling of photographic materials troublesome.

On the other hand, semiconductor laser has the advantages that the apparatus for the laser is small and inexpensive, the laser can be easily modulated, the life is longer than foregoing lasers, and also since a semi-conductor laser emits in an infrared region, a photographic material with light sensitivity in an infrared region can be used, whereby a bright safe light can be used to facilitate the handling of the photographic light-sensitive material. However, a photographic material with high sensitivity in an infrared region and excellent shelf life has not yet been developed and hence the characteristics of semiconductor laser with the foregoing excellent advantages cannot be fully utilized.

A commercially available photographic film with a sensitized infrared spectral region is, for example, HIE 135-20 made by Eastman Kodak Company but the manufacturer recommends the photographic material be stored in a cold or refrigerated state. As will be understood from these recommendations, a photographic material having sensitized infrared region has unstable sensitivity and a specific care is necessary for storage.

As a production technique for photographic light-sensitive materials, it is known to employ a spectral sensitization technique, that is, a technique of expanding the light-sensitive wave length region of a silver halide photographic emulsion to a long wave length side by incorporating certain cyanine dyes in the silver halide emulsion and also to employ this technique for sensitizing not only to light in a visible region but also in an infrared region. For spectral sensitization in an infrared region of a photographic material, sensitizing dyes having absorptions to infrared light are used and they are described in, for example, Mees; *The Theory of the Photographic Process*, 3rd Edition, pages 198–201, MacMillan Co., (1966).

In this case, it is desired for the photographic material thus sensitized to have a high spectral sensitivity, that is, a high sensitivity for infrared light and a sensitivity of the photographic material which changes least during storage. Many sensitizing dyes have been developed for this purpose. For example, sensitizing dyes are described in U.S. Pat. Nos. 2,095,854; 2,095,856; 2,955,939; 3,482,978; 3,552,974; 3,573,921; 3,582,344; etc. However, even using these sensitizing dyes, the sensitivity and the shelf life of photographic materials are still unsatisfactory.

On the other hand, it is known that the spectral sensitivity in photographic materials is greatly increased by adding certain specific organic compounds in addition to the spectral sensitizing dye and this effect is known as a super dye sensitization effect. Since the addition of an organic compound or an inorganic compound generally does not increase the sensitivity of a photographic material or decreases the sensitivity, the super dye sensitization effect is said to be a specific phenomenon but a very severe selectivity is required for the sensitizing dye and the organic or inorganic compound used for the combination. Therefore, even a slight difference in the chemical structure of the compound markedly influences the super sensitizing action and hence it is difficult to select combinations for the super sensitization from a simple estimation of suitable compounds from the chemical structures thereof. Triazine derivatives described in, for example, U.S. Pat. Nos. 2,875,058 and 3,695,888, mercapto compounds described in U.S. Pat. No. 3,457,078, thiourea compounds described in U.S. Pat. No. 3,458,318, pyrimidine derivatives described in U.S. Pat. No. 3,615,623, etc. are known as organic compounds used for super sensitization with sensitizing dyes. Also, U.S. Pat. No. 4,011,083 discloses that an infrared sensitization is achieved by using an azaindene compound and a desensitizing amount of an infrared sensitizing dye.

The techniques described in the above patents certainly increase the infrared sensitivity and improve shelf life to some extent but the effects are still unsatisfactory. Thus, super sensitizing means for further increasing infrared sensitivity and shelf life is desired.

On the other hand, when a silver halide emulsion is in a liquid state before coating, the sensitivity and fog thereof tends to change. In particular the change in sensitivity and fog caused by desorption and decomposition of sensitizing dyes tends to occur. The change in photographic characters of a silver halide emulsion in a liquid state before coating is a large problem in production of photographic materials. However, stabilizers such as 1-phenyl-5-mercaptotetrazole, etc., ordinarily used as stabiliers for silver halide photographic emulsions are ineffective to improve the stability of silver halide photographic emulsions containing infrared sensitizing dyes, which are sol states before coating. Therefore, development of a technique for specifically improving the stability of silver halide emulsions containing infrared sensitizing dyes which are in the liquid states has been desired.

SUMMARY OF THE INVENTION

An object of this invention is to provide a silver halide photographic material with high sensitivity to infrared light.

Another object of this invention is to provide a silver halide photographic material containing silver halide emulsions, where the silver halide emulsions show less change in sensitivity in liquid states before coating.

Still another object of this invention is to provide a silver halide photographic material having less change in sensitivity and fog during storage thereof.

The foregoing objects of this invention are attained by incorporating into the silver halide emulsion layer at least one of infrared sensitizing dye represented by following general formula (I)

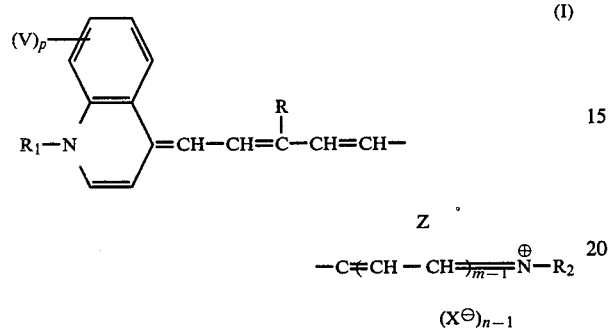

wherein $R_1$ and $R_2$, which may be the same or different, each represents an alkyl group or a substituted alkyl group; R represents a hydrogen atom, a lower alkyl group, a phenyl group or a benzyl group; V represents a hydrogen atom, a lower alkyl group, an alkoxy group, a halogen atom or a substituted alkyl group; Z represents a non-metallic atomic group necessary to form a 5- or 6-membered nitrogen-containing heterocyclic ring; X represents an acid anion; and m, n and p each represents 1 or 2; and at least one compound represented by following general formula (II)

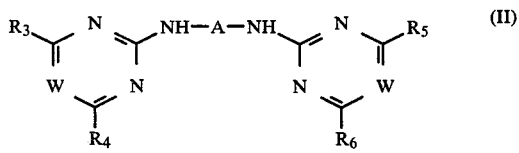

wherein A represents a divalent aromatic residue; $R_3$, $R_4$, $R_5$ and $R_6$ which may be the same or different each represents a hydrogen atom, a hydroxy group, an alkyl group, an alkoxy group, an aryloxy group, a halogen atom, a heterocyclic nucleus, a heterocyclicthio group, an arylthio group, an amino group, a substituted or unsubstituted alkylamino group, a substituted or unsubstituted arylamino group, a substituted or unsubstituted aralkylamino group, an aryl group or a mercapto group; at least one of A, $R_3$, $R_4$, $R_5$ and $R_6$ has a sulfo group; and W represents —CH= or —N=.

DETAILED DESCRIPTION OF THE INVENTION

The infrared sensitizing dyes used in this invention are shown by foregoing general formula (I), wherein $R_1$ and $R_2$ each represents an alkyl group having, preferably 1 to 8 carbon atoms, such as a methyl group, an ethyl group, a propyl group, a butyl group, a pentyl group, a heptyl group, etc., or a substituted alkyl group. Examples of suitable substituents are a carboxy group, a sulfo group, a cyano group, a halogen atom (e.g., fluorine atom, chlorine atom, bromine atom, etc.), a hydroxy group, an alkoxycarbonyl group (having 8 or less carbon atoms, such as a methoxycarbonyl group, an ethoxycarbonyl group, a benzyloxycarbonyl group, etc.), an alkoxy group (having 7 or less carbon atoms, such as a methoxy group, an ethoxy group, a propoxy group, a butoxy group, a benzyloxy group, etc.), an aryloxy group (e.g., a phenoxy group, a p-tolyloxy group, etc.), an acyloxy group (having 3 or less carbon atoms, such as an acetyloxy group, a propionyloxy group, etc.), an acyl group (having 8 or less carbon atoms, such as an acetyl group, a propionyl group, a benzoyl group, a mesyl group, etc.), a carbamoyl group (e.g., a carbamoyl group, an N,N-dimethylcarbamoyl group, a morpholinocarbamoyl group, a piperidinocarbamoyl group, etc.), a sulfamoyl group (e.g., a sulfamoyl group, an N,N-dimethylsulfamoyl group, a morpholinosulfamoyl group, etc.), an aryl group (e.g., a phenyl group, a p-hydroxyphenyl group, a p-carboxyphenyl group, a p-sulfophenyl group, an α-naphthyl group, etc.), etc. The alkyl moiety of the substituted alkyl group represented by $R_1$ or $R_2$ has, preferably, 1 to 6 carbon atoms. It is preferred that both $R_1$ and $R_2$ are an alkyl group or both $R_1$ and $R_2$ are an alkyl group having a sulfo group or an alkyl group having a carboxy group.

R in general formula (I) is a hydrogen atom, a lower alkyl group (e.g., a methyl group, an ethyl group, a propyl group, etc.), a phenyl group or a benzyl group. In a preferred embodiment, R is a lower (e.g., $C_1$-$C_4$) alkyl group or a benzyl group.

V in general formula (I) is a hydrogen atom, a lower (e.g., $C_1$-$C_4$) alkyl group (e.g., a methyl group, an ethyl group, etc.), an alkoxy group (e.g., a methoxy group, an ethoxy group, a butoxy group, etc.), a halogen atom (e.g., a fluorine atom, a chlorine atom, etc.), or a substituted alkyl group (e.g., a trifluoromethyl group, a carboxymethyl group, etc.).

Z in general formula (I) is a nonmetallic atomic group necessary to form a 5-membered or 6-membered nitrogen containing heterocyclic ring and is, for example, a thiazole nucleus (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methoxybenzothiazole, 6-methoxybenzothiazole, 5-ethoxybenzothiazole, 5-carboxybenzothiazole, 5-ethoxycarbonylbenzothiazole, 5-phenethylbenzothiazole group, 5-fluorobenzothiazole, 5-trifluoromethylbenzothiazole, 5,6-dimethylbenzothiazole, 5-hydroxy-6-methylbenzothiazole, tetrahydrobenzothiazole, 4-phenylbenzothiazole, naphtho[2,1-d]thiazole, naphtho[1,2-d]thiazole, naphtho[2,3-d]thiazole, 5-methoxy[1,2-d]thiazole, 7-ethoxynaphtho[2,1-d]thiazole, 8-methoxynaphtho[2,1-d]thiazole, 5methoxynaphtho[2,3-d]thiazole, etc.), a selenazole nucleus (e.g., benzoselenazole, 5-chlorobenzoselenazole, 5-methoxybenzoselenazole, 5-methylbenzoselenazole, 5-hydroxybenzoselenazole, naphtho[2,1-d]selenazole, naphtho [1,2-d]selenazole, etc.), an oxazole nucleus (e.g., benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-trifluorobenzoxazole, 5-hydroxybenzoxazole, 5-carboxybenzoxazole, 6-methylbenzoxazole, 6-chlorobenzoxazole, 6-methoxybenzoxazole, 6-hydroxybenzoxazole, 5,6-dimethylbenzoxazole, 4,6-dimethylbenzoxazole, 5-ethoxybenzoxazole, naphtho[2,1-d]oxazole, naphtho[1,2-d]oxazole, naphtho[2,3-d]oxazole, etc.), a quinoline nucleus (e.g., 2-quinoline, 3-methyl-2-quinoline, 5-ethyl-2-quinoline, 6-methyl-2-quinoline, 8-fluoro-2-quinoline, 6-methoxy-2-quinoline, 6-hydroxy-2-quinoline, 8-chloro-2-quinoline, etc.), a 3,3-dialkylindolenine nucleus (e.g., 3,3-dimethylindolenine, 3,3-diethylindolenine, 3,3-dimethyl-5-cyanoindolenine, 3,3-dimethyl-5-methoxyindolenine, 3,3-dimethyl-5-methylindolenine, 3,3-dimethyl-5-chloroindolenine, etc.), an imidazole nucleus (e.g., 1-methylbenzimidazole, 1-ethylbenzimidazole, 1-methyl-5-chlorobenzimidazole, 1-ethyl-5-chlorobenzimidazole, 1-methyl-5,6-dichlorobenzimidazole, 1-ethyl-5,6-dichlorobenzimidazole, 1-alkyl-5-methoxybenzimidazole, 1-methyl-5-cyanobenzimidazole, 1-ethyl-5-cyanobenzimidazole, 1-methyl-5-fluorobenzimidazole, 1-ethyl-5-fluorobenzimidazole, 1-phenyl-5,6-dichlorobenzimidazole, 1-allyl-5,6-dichlorobenzimidazole, 1-allyl-5-chlorobenzimidazole, 1-phenylbenzimidazole, 1-phenyl-5-chlorobenzimidazole, 1-methyl-5-trifluoromethylbenzimidazole, 1-ethyl-5-trifluoromethylbenzimidazole, 1-ethylnaphtho[1,2-d]imidazole, etc.), a pyridine nucleus (e.g., pyridine, 5-methyl-2-pyridine, 3-methyl-4-pyridine, etc.), etc. Of these nuclei, thiazole nuclei, selenazole nuclei, and oxazole nuclei are preferred. Furthermore, benzothiazole nuclei, naphthothiazole nuclei, naphthoselenazole nuclei, benzoselenazole nuclei, and naphthoxazole nuclei are especially preferred.

X in general formula (II) is an acid anion such as halogen (Cl$^-$, BR$^-$, I$^-$), perchlorate, thiocyanate, acetate, methylsulfate, ethylsulfate, benzenesulfonate, toluenesulfonate, etc. and m, n and p each is 1 or 2. When the dye has a betain structure, n is 1.;

Synthesis examples of dyes represented by general formula (I) used in this invention are shown below. Other dyes than those illustrated in these synthesis examples can be also easily prepared by reference to these synthesis examples.

Unless otherwise indicated, all parts, percents, ratios and the like are by weight.

SYNTHESIS EXAMPLE (1)

To 100 ml of dimethylformamide were added 4.7 g of 4-(4-N-acetylanilino-1,3-butanedienyl)-1-ethylquinolium iodide and 3.1 g of 2,5,6-trimethyl-3-(4-sulfobutyl)benzothiazolium and the mixture was heated on a steam bath. After adding dropwise 6 ml of triethylamine to the mixture, the reaction was continued for 15 minutes. The reaction mixture was cooled to room temperature (about 20°-30°C.) and crystals, formed were collected by suction filtration, washed with methanol, and recrystallized twice each time from a mixture of methanol and chloroform (1:1 by vol) to provide 3.2 g of the desired Dye (I-3). The yield was 61.5%.

$\lambda_{max}^{methanol}$: 744 n.m.
$\epsilon_{max}^{methanol}$: 1.70×10$^5$

SYNTHESIS EXAMPLE (2)

To 150 ml of ethanol were added 5.0 g of 2-(4-ethoxy-3-methyl-1,3-butadienyl)-3-ethylnaphtho[1,2-d]thiazolium 4-methylbenzenesulfonate and 2.8 g of 4-methyl-1-(4-sulfobutyl)quinolinium and the mixture was heated on a steam bath. After adding thereto dropwise 10 ml of triethylamine, the reaction was continued for 20 minutes. The reaction mixture was cooled to room temperature and crystals thus formed were collected by suction filtration, washed with methanol, and recrystallized twice each time with a mixture of methanol and chloroform to provide 3.2 g of desired Dye (I-7). The yield was 57.4%.

$\lambda_{max}^{methanol}$: 749 n.m.
$\epsilon_{max}^{methanol}$: 1.60×10$^5$

SYNTHESIS EXAMPLE (3)

To 100 ml of ethanol were added 4.0 g of 2-(4-ethoxy-3-methyl-1,3-butanedienyl)-6-methyl-3-(4-sulfobutyl)-benzothiazolium and 2.8 g of 4-methyl-1-(4-sulfobutyl)-quinolinium and the mixture was heated on a steam bath. After adding thereto dropwise 5 ml of triethylamine, the reaction was continued for 10 minutes. The reaction mixture was cooled to room temperature and a solution of 2 g of potassium acetate dissolved in 25 ml of methanol was added to the reaction mixture, whereby a semi-solid material precipitated. The supernatant liquid was removed by decantation. The residue was dissolved in methanol by heating and the solution was allowed to stand at room temperature, whereby crystals precipitated. The crystals thus formed were collected by suction filtration, washed with methanol, and recrystallized twice each time from methanol to provide 1.1 g of desired Dye (I-11). The yield was 16.5%.

$\lambda_{max}^{methanol}$: 734 n.m.
$\epsilon_{max}^{methanol}$: 1.54×10$^5$.

Specific examples of sensitizing dyes represented by general formula (I) used in this invention are illustrated below but the invention is not to be construed to be limited to these compounds.

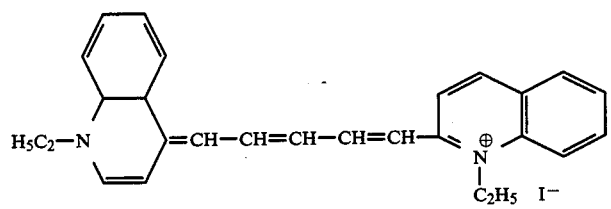

I-1

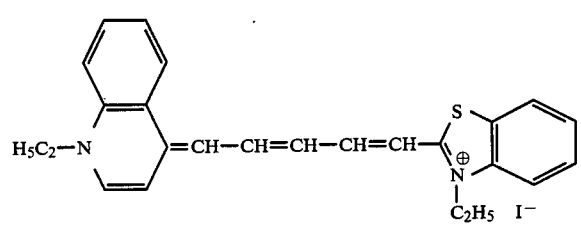

I-2

-continued
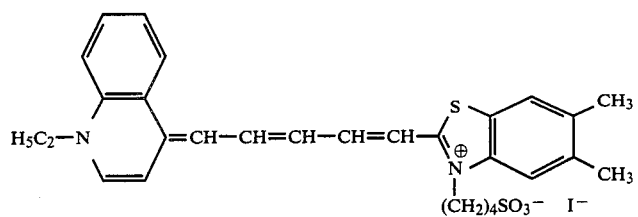
I-3
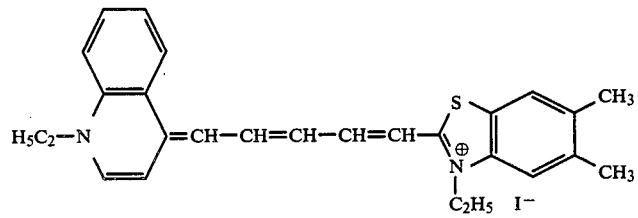
I-4
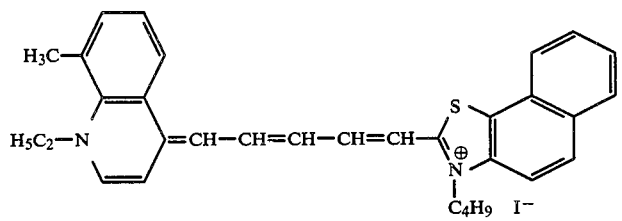
I-5
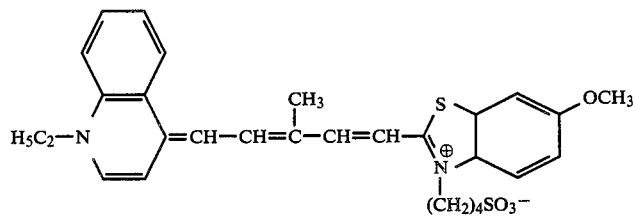
I-6
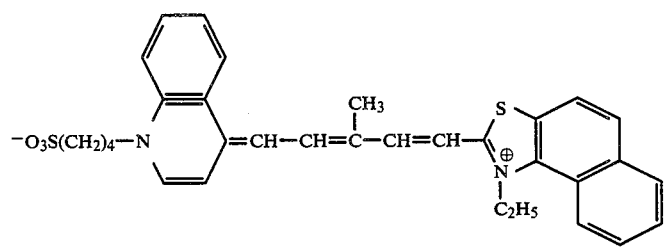
I-7
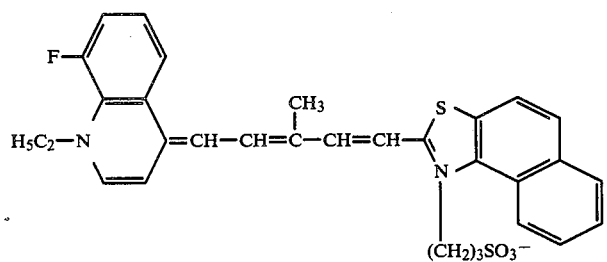
I-8

-continued
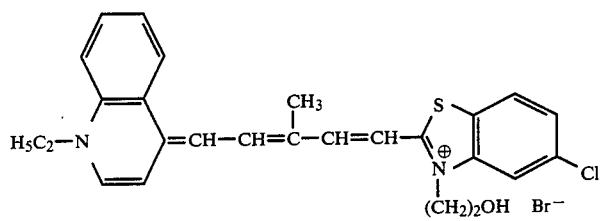
I-9
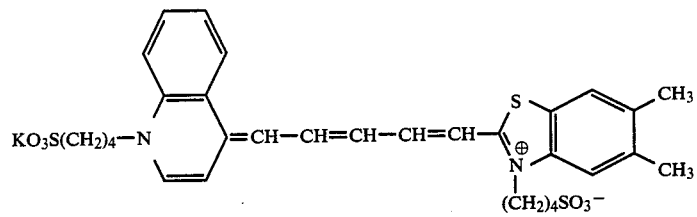
I-10
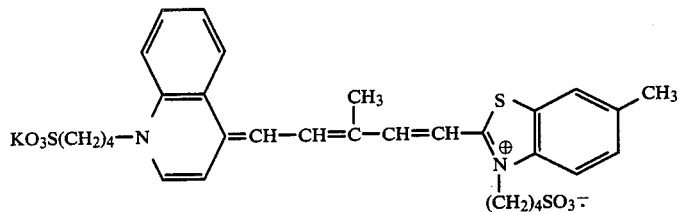
I-11
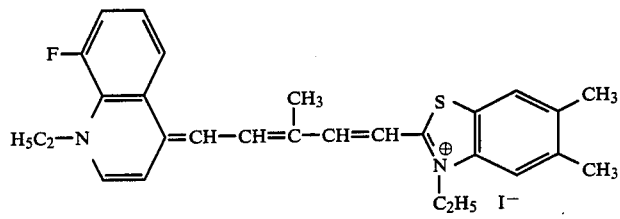
I-12
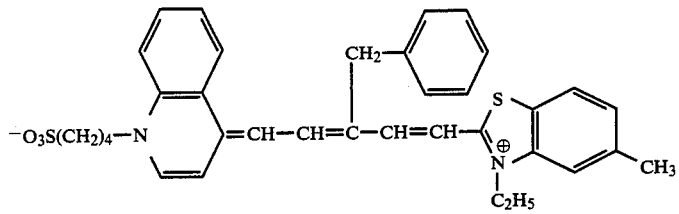
I-13
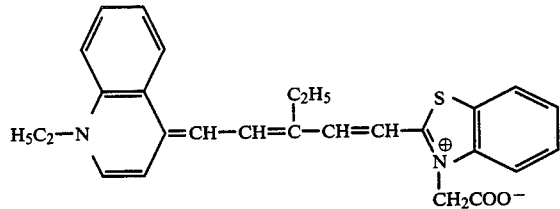
I-14
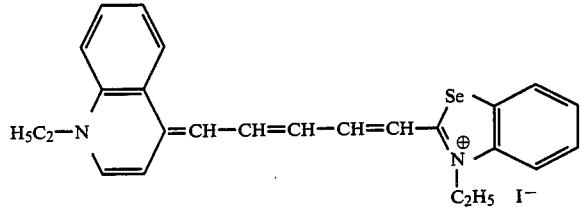
I-15

I-16

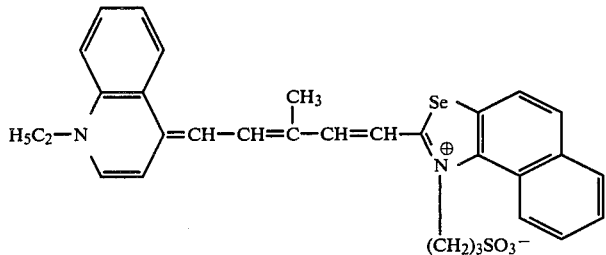

I-17

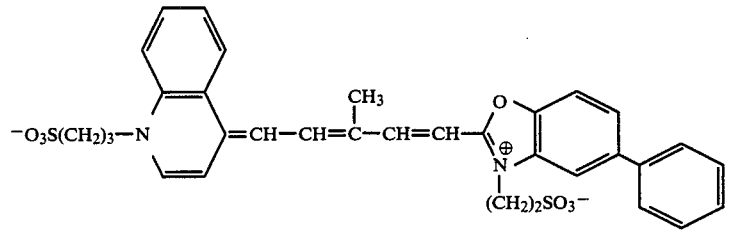

I-18

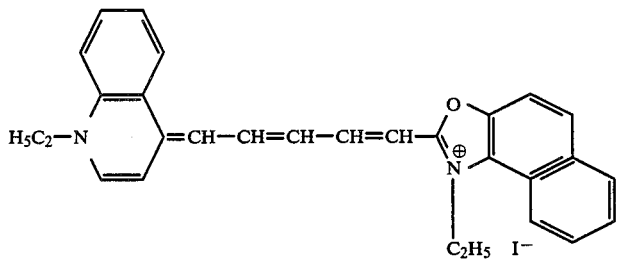

In this invention, the compound represented by general formula (II) described above is used together with the foregoing infrared sensitizing dye represented by general formula (I).

In general formula (I), —A— is a divalent aromatic residue, which may have —SO$_3$M group (wherein M represents a hydrogen atom or a cation imparting water-solubility, such as sodium, potassium, etc.).

As —A—, aromatic residues for —A$_1$— and —A$_2$— are useful but when —SO$_3$M is not present in R$_3$, R$_4$, R$_5$, or R$_6$, —A— is selected from aromatic residues for —A$_1$—.

—A$_1$—:

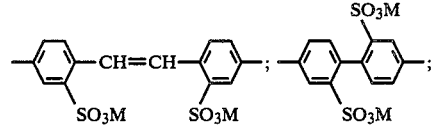 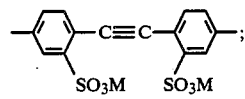

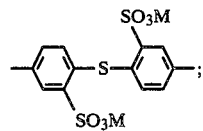

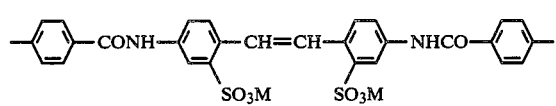 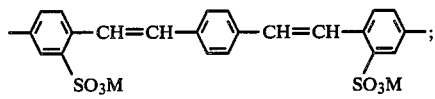

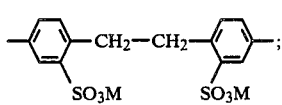 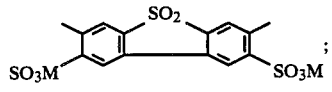

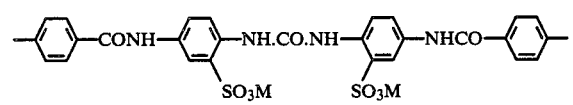

(wherein M represents a hydrogen atom or a cation imparting water-solubility).

—A$_2$—:

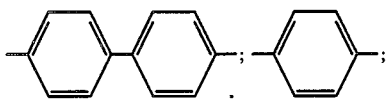

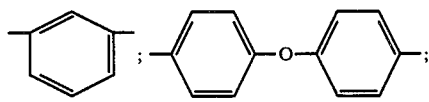

-continued

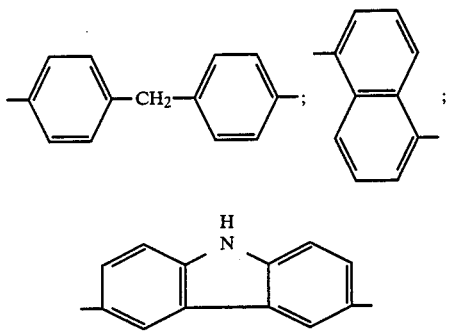

In general formula (II), R₃, R₄, R₅, and R₆ each represents a hydrogen atom, a hydroxy group, a lower alkyl group (having, preferably, 1 to 8 carbon atoms, such as a methyl group, an ethyl group, an n-propyl group, an n-butyl group, etc.), an alkoxy group (having, preferably, 1 to 8 carbon atoms, such as a methoxy group, an ethoxy group, a propoxy group, a butoxy group, etc.), an aryloxy group (e.g., a phenoxy group, a naphthoxy group, an o-tolyoxy group, a p-sulfophenoxy group, etc.), a halogen atom (e.g., a chlorine atom, a bromine atom, etc.), a heterocyclic nucleus (e.g., a morpholine group, a piperidyl group, etc.), an alkylthio group (e.g., a methylthio group, an ethylthio group, etc.), a heterocyclylthio group (e.g., a benzothiazolylthio group, a benzimidazolylthio group, a benzimidazolylthio group, a phenyltetrazolylthio group, etc.), an arylthio group (e.g., a phenylthio group, a tolylthio group, etc.), an amino group, an alkylamino group, or a substituted alkylamino group (e.g., a methylamino group, an ethylamino group, a propylamino group, a dimethylamino group, a diethylamino group, a dodecylamino group, a cyclohexylamino group, a β-hydroxyethylamino group, a di-(β-hydroxyethyl)amino group, a β-sulfoethylamino group, etc.), an arylamino group or a substituted arylamino group (e.g., an anilino group, an o-sulfoanilino group, a m-sulfoanilino group, a p-sulfoanilino group, an o-toluidino group, a m-toluidino group, a p-toluidino group, an o-carboxyanilino group, a m-carboxyanilino group, a p-carboxyanilino group, an o-chloroanilino group, a m-chloroanilino group, a p-chloroanilino group, a p-aminoanilino group, an o-anisidino group, a m-anisidino group, a p-anisidino group, an o-acetaminoanilino group, a hydroxyanilino group, a disulfophenylamino group, a naphthylamino group, a sulfonaphthylamino group, etc.), a heterocyclicamino group (e.g., a 2-benzothiazolylamino group, a 2-pyridylamino group, etc.), a substituted or unsubstituted aralkylamino group (e.g., a benzylamino group, an o-acylamino group, a m-anisylamino group, a p-anisylamino group, etc.), an aryl group (e.g., a phenyl group, etc.), or a mercapto group. R₃, R₄, R₅ and R₆ may be the same or different. When —A— is selected from the group of —A₂—, at least one of R₃, R₄, R₅, and R₆ must have at least one sulfo group (which may be in the form of a free acid group or a salt).

In general formula (II), W is —CH= or —N= and is preferably —CH=.

The compounds of the general formula (II) are disclosed in, for example, U.S. Pat. No. 3,615,632.

Specific examples of compounds represented general formula (II) are illustrated below but this invention is not limited to these compounds.

(II-1): Disodium 4,4′-bis[4,6-di(benzothiazolyl-2-thio)-pyrimidine-2-ylamino]stilbene-2,2′-disulfonate
(II-2): Disodium 4,4′-bis[4,6-di(benzothiazolyl-2-amino)pyrimidine-2-ylamino]stilbene-2,2′-disulfonate
(II-3): Disodium 4,4′-bis[4,6-di(naphthyl-2-oxy)pyrimidine-2-ylamino]stilbene-2,2′-disulfonate
(II-4): Disodium 4,4-bis[4,6-di(naphthl-2-oxy)pyrimidine-2-ylamino]bibenzyl-2,2′-disulfonate
(II-5): Disodium 4,4′-bis(4,6-dianilinopyrimidine-2-ylamino)stilbene-2,2′-disulfonate
(II-6): Disodium 4,4′-bis[4-chloro-6-(2-naphthyloxy)-pyrimidine-2-ylamino]biphenyl-2,2′-disulfonate
(II-7): Disodium 4,4′-bis[4,6-di(1-phenyltetrazolyl-5-thio)pyrimidine-2-ylamino]stilbene-2,2′-disulfonate
(II-8): Disodium 4,4′-bis[4,6-di(benzimidazolyl-2-thio)-pyrimidine-2-ylamino]stilbene-2,2′-disulfonate
(II-9): Disodium 4,4′-bis(4,6-diphenoxypyrimidine-2-ylamino)stilbene-2,2′-disulfonate
(II-10): Disodium 4,4′-bis(4,6-diphenylthiopyrimidine-2-ylamino)stilbene-2,2′-disulfonate
(II-11): Disodium 4,4′-bis(4,6-dimercaptopyrimidine-2-ylamino)biphenyl-2,2′-disulfonate
(II-12): Disodium 4,4′-bis(4,6-dianilinotriazine-2-ylamino)stilbene-2,2′-disulfonate
(II-13): Disodium 4,4′-bis(4-anilino-6-hydroxytriazine-2-ylamino)stilbene-2,2′-disulfonate
(II-14): Disodium 4,4′-bis(4-naphthylamino-6-anilino-triazine-2-ylamino)stilbene-2,2′-disulfonate.

Of these compounds illustrated above, Compounds (II-1) to (II-12) are preferred and in particular, Compounds (II-1), (II-2), (II-3), (II-4), (II-5), and (II-7) are preferred.

The sensitizing dye of general formula (I) used in this invention is incorporated in a silver halide emulsion in an amount of about $5 \times 10^{-7}$ mole to about $5 \times 10^{-3}$ mole, preferably $1 \times 10^{-6}$ to $1 \times 10^{-3}$ mole, more preferably $2 \times 10^{-6}$ to $5 \times 10^{-4}$ mole, per mole of silver halide.

The infrared sensitizing dye of general formula (I) used in this invention can be dispersed directly in a silver halide emulsion. Also, the sensitizing dye may be added to a silver halide emulsion as a solution thereof in an appropriate solvent such as methanol, ethanol, methyl Cellosolve, acetone, water, pyridine, or a mixture thereof. In this case, ultrasonic agitation may be employed in dissolving the dye in a solvent. Furthermore, the following methods can be utilized for adding the infrared sensitizing dyes of general formula (I). That is, a method of dissolving a dye in an organic solvent, dispersing the solution in an aqueous solution of a hydrophilic colloid, and adding the dispersion to a silver halide emulsion as described in U.S. Pat. No. 3,469,987; a method of dispersing a water-insoluble dye in an aqueous solvent without dissolving in an organic solvent and adding the dispersion to a silver halide emulsion as described in Japanese Patent Publication No. 24,185/'71; a method of dissolving a dye in an aqueous solution of a surface active agent and adding the solution to a silver halide emulsion as described in U.S. Pat. No. 3,822,135; a method of dissolving a dye using a compound capable of red shifting and adding the solution to a silver halide emulsion as described in Japanese Patent Publication (Unexamined) No. 74,624/'76; and a method of dissolving a dye in a substantially water free acid and adding the solution to a silver halide emulsion as described in Japanese Patent Publication (Unexamined) No. 80,826/'76 can be used. Other methods of adding dyes to silver halide emulsions which can be used in this invention are described in U.S. Pat. Nos. 2,912,343; 3,342,605; 2,996,287; 3,429,835, etc. Also, the infrared sensitizing dye of foregoing general formula (I) may be uniformly dispersed in a silver halide emulsion directly before the emulsion is coated on an appropriate support but the sensitizing dye may, as a matter of course, be dispersed in the emulsion at any desired state of producing the silver halide emulsion.

The infrared sensitizing dyes of this invention may be used in combination with other sensitizing dyes. Suitable sensitizing dyes are described in, for example, U.S. Pat. Nos. 3,703,377; 2,688,545; 3,703,377; 3,397,060; 3,615,635; and 3,628,964; U.K. Pat. Nos. 1,242,588 and 1,293,862; Japanese Patent Publication Nos. 4936/'68; 14,030/'69 and 10,773/'68; U.S. Pat. No. 3,416,927; Japanese Patent Publication No. 4930/68' U.S. Pat. Nos. 3,615,613; 3,615,623; 3,617,295 and 3,635,721.

The compound of general formula (II) used in this invention is advantageously added to a silver halide emulsion in an amount of about 0.01 g to 5 g per mole of silver halide in the silver halide emulsion.

The ratio (weight ratio) of the dye of general formula (I)/the compound of general formula (II) is, preferably 1/1 to 1/100, more preferably ½ to 1/50.

The compound of general formula (II) used in this invention can be directly dispersed in a silver halide emulsion or may be added to a silver halide emulsion as a solution in an appropriate solvent (e.g., methanol, ethanol, methyl Cellosolve, water, etc.). Moreover, the compound may be added to a silver halide emulsion as a solution or a dispersion in a colloid as in the case of adding the sensitizing dye. Also, the compound may be dispersed in a silver halide emulsion using the method described in Japanese Patent Publication (Unexamined) No. 80,119/'75.

The combination of the compound of the general formula (I) and the compound of the general formula (II) according to this invention may further contain the compound of general formula (III)

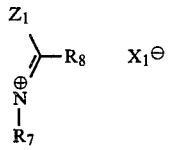

(III)

wherein $Z_1$ represents a non-metallic atomic group necessary to form a 5-membered or 6-membered nitrogen-containing heterocyclic ring, such as, for example, thiazolium (e.g., thiazolium, 4-methylthiazolium, benzothiazolium, 5-methylbenzothiazolium, 5-chlorobenzothiazolium, 5-methoxybenzothiazolium, 6-methylbenzothiazolium, 6-methoxybenzothiazolium, naphtho[1,2-d]thiazolium, naphtho[2,1-d]thiazolium, etc.), oxazolium (e.g., oxazolium, 4-methyloxazolium, benzoxazolium, 5-chlorobenzoxazolium, 5-phenylbenzoxazolium, 5-methylbenzoxazolium, naphtho[1,2-d]oxazolium, etc.), imidazolium (e.g., 1-methylimidazolium, 1-propyl-5-chlorobenzimidazolium, 1-ethyl-5,6-dichlorobenzimidazolium, 1-allyl-5-trichloromethyl-6-chlorobenzimidazolium, etc.), or selenazolium (e.g., benzoselenazolium, 5-chlorobenzoselenazolium, 5-methylbenzoselenazolium, 5-methoxybenzoselenazolium, naphtho[1,2-d]selenazolium, etc.); $R_7$ represents a hydrogen atom, an alkyl group (having 1 to 8 carbon atoms, such as a methyl group, an ethyl group, a propyl group, a butyl group, a pentyl group, etc.), an alkenyl group (e.g., an allyl group, etc.); $R_8$ represents a hydrogen atom or a lower alkyl group (e.g., a methyl group, an ethyl group, etc.); $X_1$ *represents an acid anion (e.g., $Cl^-$, $Br^-$, $I^-$, $ClO_4^-$, etc.).*

In a preferred embodiment $Z_1$ is thiazolium and is, more preferably a substituted or unsubstituted benzothiazolium or naphthothiazolium.

The compounds of the general formula (III) are disclosed in, for example, U.S. Pat. Nos. 2,131,038, 2,704,721, 3,265,498, etc.

Specific examples of compounds represented by general formula (III) are illustrated below but the invention is not to be construed as limited to these compounds.

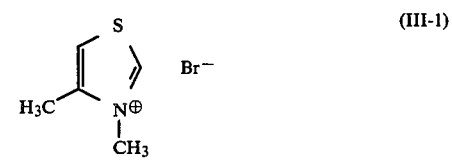

(III-1)

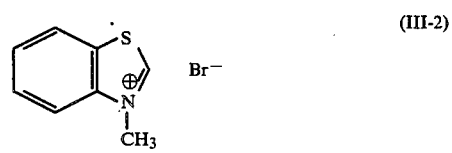

(III-2)

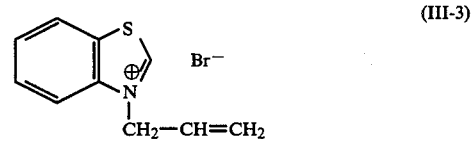

(III-3)

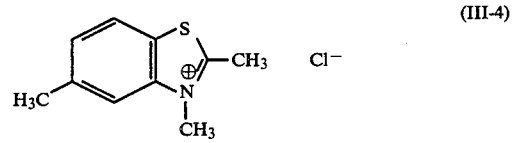

(III-4)

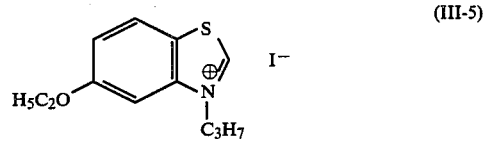

(III-5)

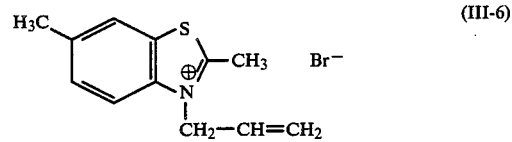

(III-6)

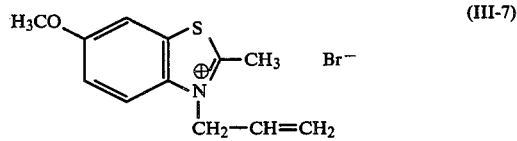

(III-7)

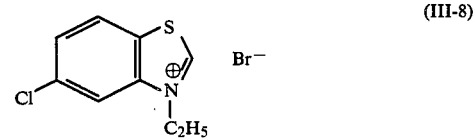

(III-8)

-continued (III-9) 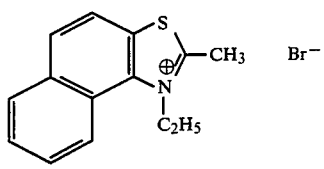

(III-10) 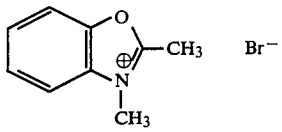

(III-11) 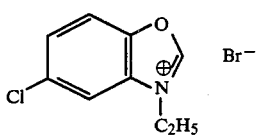

(III-12) 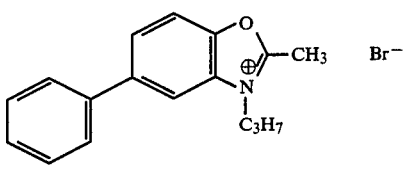

(III-13) 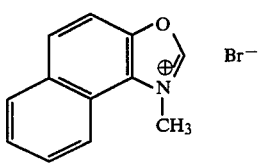

(III-14) 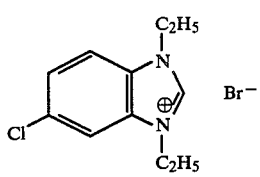

(III-15) 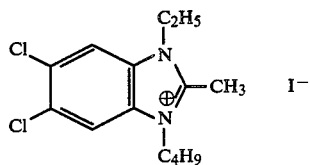

(III-16) 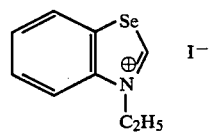

(III-17) 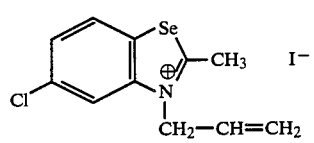

-continued (III-18)

The compound of general formula (III) is advantageously used in the silver halide emulsion in an amount of from about 0.01 g to about 5 g per mole of silver halide in the silver halide emulsion.

The ratio (weight ratio) of the infrared sensitizing dye of formula (I)/the compound of formula (III) is, preferably 1/1 to 1/300, more preferably ½ to 1/50.

The compound of general formula (III) can be directly dispersed in a silver halide emulsion or may be added to a silver halide emulsion as a solution in an appropriate solvent such as water, methanol, ethanol, propanol, methyl Cellosolve, acetone, etc., or a mixture of these solvents. Furthermore, the compound may be added to a silver halide emulsion using the same method as for the sensitizing dye to a silver halide emulsion as described hereinbefore.

The compound represented by general formula (III) may be added to a silver halide emulsion before or after the addition of the sensitizing dye represented by general formula (I). Also, a solution of the compound of general formula (I) and a solution of the sensitizing dye of general formula (I) are separately prepared and these solutions may be simultaneously added to a silver halide emulsion or may be added to the emulsion as a mixture of the solutions.

The silver halide used in this invention includes silver chloride, silver bromide, silver iodide, silver chlorobromide, silver chloroiodide, silver iodobromide, silver chloroiodo-bromide, etc. In this invention, silver chloroiodide, silver chlorobromide and silver iodobromide are particularly preferred. Also, silver chlorobromide or silver chloroiodo-bromide containing 0 to 1 mole % silver iodide is more preferred in this invention.

These silver halides may be crude grains or fine grains, or may be a mixture of these grains. The silver halide grains may be formed using known methods such as a single jet method, a double jet method, a control double jet method, etc.

Furthermore, the silver halide grains used in this invention may have a uniform crystal structure throughout the grains or may have a structure where the outside the grains has a different property from the inside thereof, or may be the so-called conversion-type grains as described in U.K. Pat. No. 635,841 and U.S. Pat. No. 3,622,318. Moreover, the silver halide may be the type forming a latent image mainly on the surface of the grains or an internal latent image type forming a latent image in the inside of the grains.

Suitable photographic silver halide emulsions are described in Mees and James, *The Theory of the Photographic Process*, published by MacMillan Co., Grafkides, *Photographic Chemistry*, published by Fountain Press Co., *Research Disclosure*, Vol. 176 (1978, 12) (RD-17643), etc., and can be prepared using an ammonia method, a neutralization method, an acid method, etc.

The mean diameter (measured by, for example, the projected area method, the number average method, etc.) of the silver halide grains is, preferably from about 0.04 μm to 4 μm, in particular less than 0.7 μm.

During the formation of the silver halide grains, a silver halide solvent such as ammonia, potassium rhodanide, ammonium rhodanide, thioether compounds (e.g., those described in U.S. Pat. Nos. 3,271,157; 3,574,628; 3,704,130; 4,397,439; 4,276,374, etc.), thion compounds (e.g., those described in Japanese Patent Publication (Unexamined) Nos. 144,319/'78; 82,408/'78; 77,737/'80, etc.), amine compounds (e.g., those described in Japanese Patent Publication (Unexamined) No. 100,717/'79, etc.), etc., can be used for controlling the growth of the silver halide grains.

Moreover, during formation, or before or after formation of silver halide grains a water-soluble rhodium compound and/or a water-soluble iridium compound may be added to the system.

The silver halide photographic emulsions used in this invention may be chemically sensitized by, for example, a gold sensitization (as described in U.S. Pat. Nos. 2,540,085; 2,597,876; 2,597,915; 2,399,083, etc.), a sensitization by a metal ion belonging to group VIII of the periodic table (as described in U.S. Pat. Nos. 2,448,060; 2,540,086; 2,566,245; 2,566,263; 2,598,079, etc.), a sulfur sensitization (as described in U.S. Pat. Nos. 1,574,944; 2,278,947; 2,440,206; 2,521,926; 3,021,215; 3,038,805; 2,410,689; 3,189,458; 3,415,649; 3,635,717, etc.), a reduction sensitization (as described in U.S. Pat. Nos. 2,518,698; 2,419,974; and 2,983,610, Research Disclosure, Vol. 176 (1978, 12) (RD-17643), Paragraph III), a sensitization by thioether compounds (as described in U.S. Pat. Nos. 2,521,926; 3,021,215; 3,038,805; 3,046,129; 3,046,132; 3,046,133; 3,046,134; 3,046,135; 3,057,724; 3,062,646; 3,165,552; 3,189,458; 3,192,046; 3,506,443; 3,671,260; 3,574,704; 3,625,697; 3,635,717; 4,198,240, etc.), or a combination of these sensitization methods.

Suitable examples of the chemical sensitizers are a sulfur sensitizer such as allyl thiocarbamide, thiourea, sodium thiosulfate, thioether, cystine, etc.; a noble metal sensitizer such as potassium chloroaurate, aurous thiosulfate, potassium chloropalladate, etc.; a reduction sensitizer such as tin chloride, phenylhydrazine, reductone, etc.

Other examples of the chemical sensitizers which can be used in this invention are polyoxyethylene derivatives (e.g., U.K. Pat. No. 981,470; Japanese Patent Publication No. 6475/'56, U.S. Pat. No. 2,716,062, etc.), polyoxypropylene derivatives, and derivatives having a quaternary ammonium group.

The photographic silver halide emulsions used in this invention may contain various additives for preventing a reduction in sensitivity and the formation of fog during the production of the photographic light-sensitive materials and during the storage or processing of the photographic materials. Such additives are nitrobenzimidazole, ammonium chloroplatinate, 4-hydroxy-6-methyl-1,3,3a,7-tetraazaindene, 1-phenyl-5-mercaptotetrazole, various heterocyclic compounds, mercury-containing compounds, mercapto compounds, metal salts, etc. Examples of the compounds used in this invention are the compounds described in C. E. K. Mees, *The Theory of the Photographic Process*, 3rd Edition, pages 344–349, (1966) as well as the thiazolium salts described in U.S. Pat. Nos. 2,131,038; 2,694,716, etc.; the azaindenes described in U.S. Pat. Nos. 2,886,437; 2,444,605, etc.; urazoles described in U.S. Pat. No. 3,287,135; the sulfocatechols described in U.S. Pat. No. 3,236,652, etc.; the oximes described in U.K. Pat. No. 623,448; the mercaptotetrazoles described in U.S. Pat. Nos. 2,403,927; 3,266,897; 3,397,987, etc.; nitroindazoles; the polyvalent metal salts described in U.S. Pat. No. 2,839,405; the thiuronium salts described in U.S. Pat. No. 3,220,839; and the salts of palladium, platinum, and gold described in U.S. Pat. Nos. 2,566,263; 2,597,915, etc.

The silver halide photographic emulsions used in this invention may further contain developing agents such as hydroquinones, catechols, aminophenols, 3-pyrazolidones, ascorbic acid and derivatives thereof, reductones, phenylenediamines. They may be present in the silver halide emulsions alone or as a combination thereof. The developing agent may be present in silver halide emulsion layers and/or other photographic layers (e.g., a protective layer, an interlayer, a filter layer, an antihalation layer, a backing layer, etc.). The developing agent can be added to a coating composition for the foregoing layer of a photographic material as a solution in an appropriate solvent or as a dispersion as described in U.S. Pat. No. 2,592,368 and French Pat. No. 1,505,778.

The compounds described in, for example, U.S. Pat. Nos. 3,288,612; 3,333,959; 3,345,175; 3,708,303; U.K. Pat. No. 1,098,748; West German Pat. Nos. 1,141,531 and 1,183,784 can be used as development accelerators.

The silver halide emulsion layers can be hardened in an ordinary manner. Examples of hardening agents which can be used for the purpose in this invention are aldehyde compounds such as formaldehyde, glutaraldehyde, etc.; ketone compounds such as diacetyl, cyclopentanedione, etc.; compounds having a reactive halogen such as bis(2-chloroethylurea), 2-hydroxy-4,6-dichloro-1,3,5-triazine, and the compounds as described in U.S. Pat. Nos. 3,288,775 and 2,732,303; U.K. Pat. Nos. 974,723; 1,167,207, etc.; compounds having a reactive olefin group such as divinylsulfone, 5-acetyl-1,3-diacryloylhexahydro-1,3,5-triazine, and the compounds as described in U.S. Pat. Nos. 3,635,718 and 3,232,763; U.K. Pat. No. 994,869, etc.; N-methylol compounds such as N-hydroxymethyl phthalimide and the compounds as described in U.S. Pat. Nos. 2,732,316; 2,586,168, etc.; the isocyanates as described in U.S. Pat. No. 3,103,437, etc.; the aziridine compounds as described in U.S. Pat. Nos. 3,017,280; 2,983,611, etc.; the acid derivatives as described in U.S. Pat. Nos. 2,725,294; 2,725,295, etc.; the carbodiimide compounds as described in U.S. Pat. No. 3,100,704, etc.; the epoxy compounds as described in U.S. Pat. No. 3,091,537; the isooxazole compounds as described in U.S. Pat. Nos. 3,321,313; 3,542,292, etc.; halocarboxyaldehydes such as mucochloric acid, etc.; dioxane derivatives such as dihydroxy dioxane, dichlorodioxane, etc; and inorganic hardening agents such as chromium alum, zirconium sulfate, etc.

Also, in place of the foregoing compounds, precursors thereof, such as alkali metal bisulfite aldehyde addition products, methylol derivatives of hydantoin, primary aliphatic nitro alcohols, etc., can be used.

The silver halide photographic emulsions used in this invention may further contain surface active agents, alone or as a mixture thereof. These surface active agents are generally used as a coating aid but are also used for other purposes, for example, for emulsified dispersion, improvement of sensitized photographic characteristics, antistatic prevention, adhesion prevention, etc. Suitable surface active agents include natural surface active agents such as saponin; nonionic surface active agents such as alkylene oxide series surface active agents, glycerol series surface active agents, glycidol series surface active agents, etc; cationic surface active agents such as higher alkylamines, quaternary ammonium salts, pyridine and other heterocyclic rings, phosphoniums, sulfoniums, etc.; anionic surface active agents containing an acid group such as a carboxylic acid, sulfonic acid, phosphoric acid, a sulfuric acid ester group, a phosphoric acid ester group, etc.; and amphoteric surface active agents such as aminoacids, aminosulfonic acids, sulfuric acid esters or phosphoric acid esters of an aminoalcohol, etc.

The silver halide photographic emulsions used in this invention may further contain acylated gelatin such as phthalated gelatin, malonated gelatin, etc.; a cellulose compound such as hydroxyethyl cellulose, carboxymethyl cellulose, etc.; a soluble starch such as dextrin, etc.; or a hydrophilic polymer such as polyvinyl alcohol, polyvinyl pyrrolidone, polyacrylamide, polystyrenesulfonic acid, etc., as a protective colloid in addition to gelatin.

In this invention, it is preferred to use a polyalkylene oxide compound such as a condensation product of a polyalkylene oxide composed of at least 10 units of alkylene oxide having 2–4 carbon atoms, such as ethylene oxide, propylene-1,2-oxide, butylene-1,2-oxide, etc., preferably ethylene oxide and a compound having at least an active hydrogen atom, such as water, an aliphatic alcohol, an aromatic alcohol, a fatty acid, an organic amine, a hexitol derivative, etc., or a block copolymer of two or more kinds of polyalkylene oxides. Specific examples of polyalkylene oxide compounds used in this invention are as follows;

polyalkylene glycols,
polyalkylene glycol alkyl ethers,
polyalkylene glycol alkylaryl ethers,
polyalkylene glycol esters,
polyalkylene glycol fatty acid amides,
polyalkylene glycol amines,
polyalkylene glycol block copolymers,
polyalkylene glycol graft polymer, etc.

It is necessary for the molecular weight of the polyalkylene oxide compound to be higher than 600.

The polyalkylene oxide compound used in this invention may contain not only one but also two or more polyalkylene oxide chains. In the latter case, each polyalkylene oxide chain may be composed of less than 10 polyalkylene oxide units but the sum of the alkylene oxide units in the molecule must be at least 10. When the molecule has two or more polyalkylene oxide chains, each polyoxyalkylene oxide chain may be composed of different alkylene oxide units, such as, for example, ethylene oxide and propylene oxide. It is preferred for the polyalkylene oxide compound used in this invention to contain 14 to 100 alkylene oxide units.

Specific examples of the polyalkylene oxide compound (IV) used in this invention are as follows:

| | |
|---|---|
| HO(CH$_2$CH$_2$O)$_{90}$H | IV-1 |
| C$_4$H$_9$O(CH$_2$CH$_2$O)$_{15}$H | IV-2 |
| C$_{12}$H$_{25}$O(CH$_2$CH$_2$O)$_{15}$H | IV-3 |
| C$_{18}$H$_{37}$O(CH$_2$CH$_2$O)$_{15}$H | IV-4 |
| C$_{18}$H$_{37}$O(CH$_2$CH$_2$O)$_{40}$H | IV-5 |
| C$_8$H$_{17}$CH=CHC$_8$H$_{16}$O(CH$_2$CH$_2$O)$_{15}$H | IV-6 |

-continued

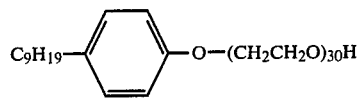
IV-7

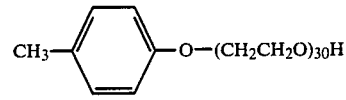
IV-8

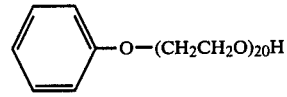
IV-9

C$_{11}$H$_{23}$COO(CH$_2$CH$_2$O)$_{80}$H    IV-10

C$_{11}$H$_{23}$COO(CH$_2$CH$_2$O)$_{24}$OCC$_{11}$H$_{23}$    IV-11

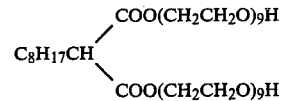
IV-12

C$_{11}$H$_{23}$CONH(CH$_2$CH$_2$O)$_{15}$H    IV-13

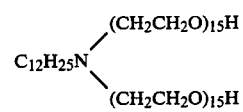
IV-14

C$_{14}$H$_{29}$N(CH$_2$)(CH$_2$CH$_2$O)$_{24}$H    IV-15

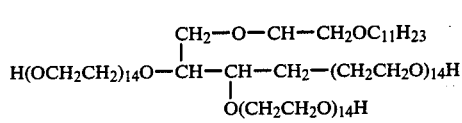
IV-16

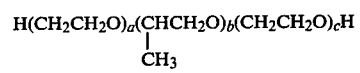
IV-17 a + b + c = 50
b:a + c = 10:9

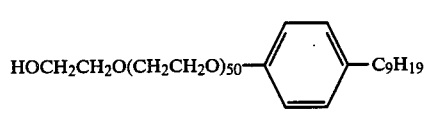
IV-18

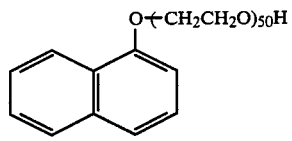
IV-19

HO(CH$_2$CH$_2$O)$_a$(CH$_2$CH$_2$CH$_2$CH$_2$O)$_b$(CH$_2$CH$_2$O)$_c$H    IV-20
a + c = 30, b = 14

HO(CH$_2$CH$_2$O)$_a$(CHCH$_2$O)$_b$(CH$_2$CH$_2$O)$_c$H    IV-21

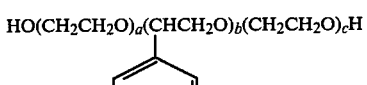

b = 8, a + c = 50

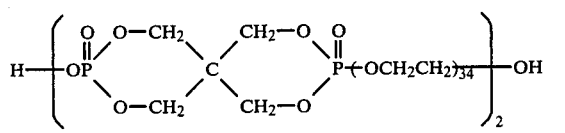

IV-22

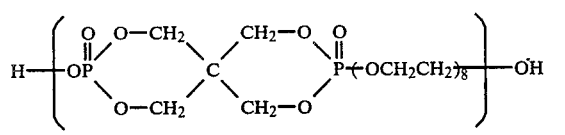

IV-23

$$HO+CH_2CH_2O+_{34}H \quad \text{IV-24}$$

The foregoing polyalkylene oxide compounds are described in Japanese Patent Publication (unexamined) Nos. 156,423/'75; 108,130/'77 and 3217/'78. The polyalkylene oxide compounds may be used alone or as a combination thereof.

For adding the polyalkylene oxide compound to a silver halide emulsion, the compound is dissolved in water or a low-boiling organic solvent miscible with water and the solution is added to a silver halide emulsion before coating, preferably after chemical ripening of the emulsion. The polyalkylene oxide compound is used in the range of $1 \times 10^{-5}$ to $1 \times 10^{-2}$ mol.

The silver halide photographic emulsion used in this invention may further contain a polymer latex composed of a homopolymer or copolymer of an alkyl acrylate, an alkyl methacrylate, acrylic acid, glycidyl acrylate, etc., as described in U.S. Pat. Nos. 3,411,911; 3,411,912; 3,142,568; 3,325,286; and 3,547,650 and Japanese Patent Publication No. 5331/'70 for improving the dimensional stability and the layer properties of the photographic material.

The siliver halide photographic emulsions used in this invention may further contain an antifoggant, a plasticizer, an optical whitening agent, an air fog preventing agent, a color toning agent, etc.

The silver halide photographic emulsions used in this invention can contain color couplers such as cyan couplers, magenta couplers, and yellow couplers and compounds for dispersing these couplers.

That is, the silver halide emulsions may contain compounds capable of formula a color by oxidative coupling with an aromatic primary amino developing agent (e.g., phenylenediamine derivatives, aminophenol derivatives, etc.) as a result of the color development process. These couplers are preferably non-diffusible couplers having a hydrophobic group, as a ballast group, in the molecule. The couplers may be four-equivalent or two-equivalent couplers. Also, the couplers may be colored couplers having a color correction effect or may be the so-called DIR couplers, i.e., couplers releasing a development inhibitor as development progress.

Furthermore, the silver halide emulsions may contain colorless DIR coupling compounds, the coupling reaction products of which are colorless, which release development inhibitors.

Moreover, in this invention, color images can be formed by developing the photographic materials with a color developer containing a diffusible coupler.

Also, the silver halide emulsions used in this invention may contain, as desired, irradiation preventing dyes as described in, for example, Japanese Patent Publication Nos. 20,389/'66; 3504/'68; and 13,168/'78 and U.S. Pat. Nos. 2,697,037; 3,423,207; and 2,865,752; U.K. Pat. Nos. 1,030,392; 1,100,546, etc.

This invention can be employed not only to sensitize black and white silver halide photographic emulsions but also to sensitize silver halide emulsions used for various color photographic materials.

The light exposure for obtaining photographic image may be performed using ordinary methods. That is, the exposure may be performed using various light sources containing infrared light such as natural light (sun light), a tungsten lamp, a mercury lamp, a xenon arc lamp, a carbon arc lamp, a xenon flash lamp, a cathode ray tube flying spot, a luminous diode, and laser light (e.g., gas laser, YAG laser, dye laser, semiconductor laser, etc.). The exposure may be also performed by light emitted from a phosphor excited by electron beams, X-rays, $\gamma$-rays, $\alpha$-rays, etc. The exposure time may be, as a matter of course, from 1/1000 sec. to 1 sec. as in ordinary camera, or may be shorter than 1/1000 sec., for example $1/10^4$ to $1/10^6$ as the case of using a xenon flash lamp or a cathode ray tube, or may be longer than 1 sec. If necessary, the spectral composition of light used for the exposure may be controlled using color filters.

The silver halide photographic emulsions used in this invention are coated on a support together with, if desired, other photographic layers. In this case, the emulsions can be coated on a support using various coating methods such as a dip coating method, an air knife coating method, a curtain coating method or an extrusion coating method using a hopper described in U.S. Pat. No. 2,681,294.

If desired, two or more layers may be simultaneously coated on a support using the method described in, for example, U.S. Pat. Nos. 2,761,791; 3,508,947; 2,941,898; 3,526,528, etc.

The finished silver halide emulsions are coated on an appropriate support. Suitable supports which can be used in this invention include a flat material undergoing no severe dimensional change during photographic processing, for example a rigid material such as glass, metal, porcelain, etc., depending on the purpose or a flexible support. Typical flexible supports include a cellulose nitrate film, a cellulose acetate film, a cellulose acetate butyrate film, a cellulose acetate propionate film, a polystyrene film, a polyethylene terephthalate film, a polycarbonate film, the laminates of these films, a thin glass sheet, papers, etc. Furthermore, a baryta-coated paper, a paper coated or laminated with an $\alpha$-olefin polymer, in particular a polymer of an $\alpha$-olefin having 2 to 10 carbon atoms, such as polyethylene, polypropylene, an ethylene-butene copolymer, etc., or a synthetic resin film having a matted surface for improving adhesion with other polymers and improving printability as described in Japanese Patent Publication No. 19,068/'72 may be also used as a support in this invention.

The support may be transparent or opaque depending on the purpose of the photographic material. In the case of a transparent support, it may be colorless or may be colored with a dye or pigment as practiced in X-ray films and as described in J. SMPTE. Vol. 67, 296 (1958).

Suitable opaque supports include a paper which is ordinarily opaque as well as an opaque film prepared by incorporating a pigment such as titanium oxide, etc., or a dye in a transparent film, a synthetic resin film surfacetreated using the method as shown in Japanese Patent Publication No. 19,068/'72, and a paper or a synthetic resin film which is completely rendered light-shielding by the addition of carbon black, a dye, etc. When the adhesion between the support and a silver halide photographic emulsion layer is insufficient, a layer having good adhesivity to the support and the emulsion layer may be formed on the support as a subbing layer. Also, the surface of the support may be subjected to a pretreatment such as a corona discharge, ultrasonic irradiation, flame treatment, etc., for further improving the adhesive property of the support.

The photographic material of this invention may be processed using ordinary processes. Known processing solutions can be used for processing the photographic material of this invention. The processing temperature is usually from about 18° C. to about 50° C. but the processing temperature may be lower than 18° C. or higher than 50° C. In this invention, a development process forming a silver image (black and white development process) or a color photographic process for forming dye images can be used depending on the purpose.

The developer used for black and white development processing can contain a known developing agent. Dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolidones, ascorbic acid, and the heterocyclic compounds formed by the condensation of 1,2,3,4-tetrahydroquinoline rings and indolenone rings as described in U.S. Pat. No. 4,067,872 can be used alone or as a combination thereof as such a developing agent. The developers may further contain preservatives, alkalizing agents, pH buffers, antifoggants, etc. The developers may further contain, if desired, dissolution assistants, color toning agents, development accelerators, surface active agents, defoaming agents, water softeners, tackifiers, etc.

The so-called "lithographic type" development process can be applied to the silver halide photographic emulsions of this invention. The term "lithographic type" developing process means a development process of infectiously performing a development in a low sulfite ion concentration employing usually a dihydroxybenzene as the developing agent for the photographic reproduction of line images or the photographic reproduction of a half tone image by dots. Details of this type of development process is described in Mason, *Photographic Processing Chemistry*, 163–165 (1966).

A fix solution with a known composition can be used for the photographic material of this invention.

Thiosulfates, thiocyanates, as well as organic sulfur compounds having the effect as a fixing agent can be used as a fixing agent for the fix solution in this invention. The fix solution may contain a water-soluble aluminum salt as a hardening agent, if desired.

An ordinary process can be employed in forming dye images. For example, a negative-positive color process (described in e.g., *Journal of the Society of Motion Picture and Television Engineers*, Vol. 61, 667–701 (1953), a color reversal process of obtaining positive dye images by developing a photographic material with a developer containing a black and white developing agent to form a negative silver image, applying at least one overall light exposure or a proper fogging treatment, and then performing a color development, and a silver dye bleaching process of forming a silver image by developing silver halide photographic emulsion layers containing dyes after image exposure and bleaching dyes using the silver image as the bleaching catalyst can be used. Details of these color developing processes are described in L. F. A. Mason, *Photographic Processing Chemistry*, pages 226–229, published by Focal Press-London, 1966. These color developing processing may be used with 3-pyrazolidones.

The color developers used in this invention may further contain various additives.

The silver halide photographic emulsions used in this invention can be fixed in a conventional manner after development and are bleached in certain cases. The bleach process may be performed simultaneous with or separate from the fix process. When bleaching and fixing are performed at the same time, a blix bath containing a bleaching agent and a fixing agent may be used.

This invention can be also employed for low-silver photographic material wherein the content of silver halide is ½ to 1/100 of that of an ordinary photographic material.

The following examples are given to further illustrate this invention in greater detail but not intended to limit the invention in any way.

EXAMPLE 1

A silver halide emulsion formed by a double jet method was physically ripened, subjected to a desalting treatment, and chemically ripened to provide a silver iodobromide emulsion (iodide content: 2.5 mole %). The mean diameter of the silver halide grains in the silver halide emulsion was about 0.6 micron. The silver halide emulsion contained about 0.65 mole of silver halide per kg of the emulsion.

After melting 1 kg of the silver halide emulsion with heating a specific amount of a methanol solution of the sensitizing dye represented by general formula (I) and a specific amount of a methanol solution of the compound represented by general formula (II) were added to the emulsion and the mixture was stirred. Then, after further adding thereto 28 ml of an aqueous solution of 1.0% by weight 1-hydroxy-3,5-dichlorotriazine sodium salt and then 40 ml of an aqueous solution of 1.0% by weight sodium dodecylbenzenesulfonate, the mixture was stirred. The finished silver halide emulsion was coated on a cellulose triacetate film support in a dry thickness of 5 microns and dried to produce a photographic film sample. The sample film was exposed through a dark red filter (SC-70) made by Fuji Photo Film Co., Ltd., using an actinometer having a light source of a color temperature of 2,854° K. After exposure, the photographic sample was developed using a developer having the following composition for 3 minutes at 20° C., processed in a stop bath and a fix bath, and then washed with water to provide a strip having a definite black image. The density of the image was measured using a p-type densitometer made by Fuji Photo Film Co., Ltd., to determine sensitivity and fog. The standard point of the optical density for determining the sensitivity was fog+0.3.

Developer Composition:
 Water: 500 ml
 N-Methyl-p-aminophenol: 2.2 g
 Sodium Sulfite (Anhydrous): 96.0 g
 Hydroquinone: 8.8 g
 Sodium Carbonate (monohydrate): 56.0 g
 Potassium Bromide: 5.0 g
 Water to make: 1 liter The results obtained are shown in Table 1 below as relative values. From these results, it can be seen that the combination of this invention provides a photographic material having a high sensitivity and with less fog as compared to a photographic material containing only the dye.

The film sample thus prepared was exposed through an optical wedge and a dark red filter, SC-66 (made by Fuji Photo Film Co., Ltd.), developed in the developer having the following composition, and then stopped, fixed, and washed with water.

The density of the image thus obtained was measured

TABLE 1

| No. | Sensitizing Dye of Formula (I) | Amount Used ($\times 10^{-6}$ mol/ kg-emulsion) | Compound of Formula (II) | Amount Used ($\times 10^{-6}$ mol/ kg-emulsion) | Relative Sensitivity | Fog |
|---|---|---|---|---|---|---|
| 1 | (I-1) | 30 | — | — | 100 (standard) | 0.08 |
| 2 | " | 30 | (II-1) | 100 | 372 | 0.08 |
| 3 | " | 30 | " | 200 | 468 | 0.07 |
| 4 | (I-3) | 30 | — | — | 100 (standard) | 0.08 |
| 5 | " | 30 | (II-1) | 100 | 479 | 0.07 |
| 6 | " | 30 | " | 200 | 617 | 0.07 |
| 7 | (I-6) | 30 | — | — | 100 (standard) | 0.08 |
| 8 | " | 30 | (II-1) | 100 | 380 | 0.08 |
| 9 | " | 30 | " | 200 | 501 | 0.08 |
| 10 | (I-9) | 30 | — | — | 100 (standard) | 0.08 |
| 11 | " | 30 | (II-1) | 100 | 490 | 0.08 |
| 12 | " | 30 | " | 200 | 513 | 0.07 |
| 13 | (I-15) | 30 | — | — | 100 (standard) | 0.08 |
| 14 | " | 30 | (II-1) | 100 | 457 | 0.07 |
| 15 | " | 30 | " | 200 | 589 | 0.07 |
| 16 | (I-18) | 30 | — | — | 100 (standard) | 0.08 |
| 17 | " | 30 | (II-1) | 100 | 363 | 0.08 |
| 18 | " | 30 | " | 200 | 490 | 0.08 |

EXAMPLE 2

To an aqueous solution of 75 g of gelatin were added an aqueous solution of 1 kg of silver nitrate and an aqueous solution of 210 g of potassium bromide and 290 g of sodium chloride simultaneously at a definite rate over a period of 35 minutes. Then, after removing insoluble salts, an aqueous solution of gelatin was added and then the mixture was chemically ripened to produce a silver chlorobromide emulsion (grain size: 0.24 micron; 30 mole % Br). To the emulsion was added 4-hydroxy-6-methyl-1,3,3a-tetraazaindene.

To the silver halide emulsion thus prepared were added the sensitizing dye of general formula (I) and the compound of general formula (II) (and the compound of general formula (III)) and after adding thereto 1-hydroxy-3,5-dichlorotriazine sodium salt as a hardening agent and sodium dodecylbenzenesulfonate as a coating aid, the emulsion was coated on a polyethylene terephthalate film at a silver coverage of 3.9 g/m$^2$.

using a p-type densitometer, made by Fuji Photo Film Co., Ltd. to determine sensitivity and fog. The standard point of the optical density for determing sensitivity was the point of fog+0.5. The results obtained are shown in Table 2.

Developer Composition:
  p-Methylaminophenyl hemisulfate: 0.31 g
  Sodium Sulfate (anhydrous): 39.6 g
  Hydroquinone: 6.0 g
  Sodium Carbonate (Anhydrous): 18.7 g
  Potassium Bromide: 0.86 g
  Citric Acid: 0.68 g
  Potassium Matahydrogensulfite: 1.5 g
  Water added to make: 1 liter From the results shown in Table 2 below, it can be seen that the combination of this invention provides a high sensitivity as compared to the comparison dye or the case of using the dye alone. Also, by the addition of the compound of general formula (II), a higher sensitivity is obtained.

TABLE 2

| No. | Sensitizing Dye of Formula (I) | Amount Used ($\times 10^{-6}$ mol/kg-emulsion) | Compounds of Formulae (II) and (III) and Amount Used Thereof (Amount: $\times 10^{-6}$ mol/kg-emulsion) | | Relative Sensitivity | Fog |
|---|---|---|---|---|---|---|
| 1 | I-4 | 30 | — | — | 100 (standard) | 0.05 |
| 2 | I-4 | 60 | — | — | 83 | 0.05 |
| 3 | I-4 | 30 | II-3 200 | — | 692 | 0.05 |
| 4 | I-4 | 60 | II-3 200 | — | 759 | 0.05 |
| 5 | I-4 | 60 | II-3 200 | III-2 120 | 933 | 0.04 |
| 6 | I-4 | 60 | II-3 200 | III-2 240 | 977 | 0.04 |
| 7 | I-4 | 30 | II-5 200 | — | 646 | 0.05 |
| 8 | I-4 | 60 | II-5 200 | — | 724 | 0.05 |
| 9 | I-4 | 60 | II-5 200 | III-2 120 | 871 | 0.04 |
| 10 | I-4 | 60 | II-5 200 | III-2 240 | 912 | 0.04 |
| 11 | I-4 | 30 | II-12 200 | — | 457 | 0.05 |
| 12 | I-4 | 60 | II-12 200 | — | 513 | 0.05 |
| 13 | I-4 | 60 | II-12 200 | III-2 120 | 603 | 0.05 |
| 14 | I-4 | 60 | II-12 200 | III-2 240 | 631 | 0.04 |
| 15 (Comparative Example) | I-4 | 60 | II-3 200 | Compound A 120 | 741 | 0.05 |
| 16 (Comparative Example) | I-4 | 60 | II-3 200 | Compound A 240 | 724 | 0.05 |
| 17 (Comparative Example) | Dye A | 30 | — | — | 83 | 0.06 |

TABLE 2-continued

| No. | Sensitizing Dye of Formula (I) | Amount Used ($\times 10^{-6}$ mol/kg-emulsion) | Compounds of Formulae (II) and (III) and Amount Used Thereof (Amount: $\times 10^{-6}$ mol/kg-emulsion) | | Relative Sensitivity | Fog |
|---|---|---|---|---|---|---|
| 18 (Comparative Example) | | 60 | — | — | 78 | 0.06 |
| 19 (Comparative Example) | Dye A | 30 | II-3 200 | — | 138 | 0.06 |
| 20 (Comparative Example) | | 60 | II-3 200 | — | 141 | 0.06 |
| 21 (Comparative Example) | Dye A | 60 | II-3 200 | III-2 120 | 141 | 0.06 |
| 22 (Comparative Example) | | 60 | II-3 200 | III-2 240 | 135 | 0.06 |

Dye A

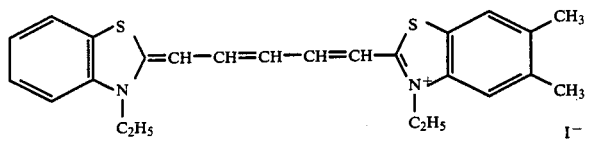

Compound A

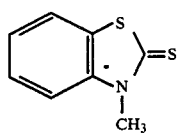

EXAMPLE 3

A part of the film samples prepared in the same manner as in Example 2 were stored for 3 days under a high-temperature and high-humidity condition (50° C., 75% RH) and then subjected to the light exposure, development, stop process, fix process, water washing, and drying as described above. The results obtained are shown in Table 3 below.

TABLE 3

| | | | Compounds of Formulae (II) and (III) and Amount Used Thereof (Amount: $\times 10^{-6}$ mol/ kg-emulsion) | | Preserved at Room Temperature (20° C., 60% RH) | | Preserved at High Temperature and High Humidity (50° C., 75% RH) | |
|---|---|---|---|---|---|---|---|---|
| No. | Sensitizing Dye of Formula (I) | Amount Used ($\times 10^{-6}$ mol/ kg-emulsion) | | | Relative Sensitivity | Fog | Relative Sensitivity | Fog |
| 1 | I-7 | 50 | — | — | 100 (standard) | 0.05 | 45 | 0.07 |
| 2 | " | 50 | II-2 150 | — | 603 | 0.05 | 575 | 0.06 |
| 3 | " | 50 | II-2 300 | — | 631 | 0.04 | 603 | 0.05 |
| 4 | " | 50 | — | III-3 180 | 135 | 0.05 | 126 | 0.05 |
| 5 | " | 50 | II-2 120 | III-3 180 | 813 | 0.04 | 794 | 0.04 |
| 6 | " | 50 | II-2 300 | III-3 180 | 851 | 0.04 | 832 | 0.04 |
| 7 | I-12 | 50 | — | — | 100 (standard) | 0.05 | 43 | 0.07 |
| 8 | " | 50 | II-2 150 | — | 646 | 0.05 | 631 | 0.06 |
| 9 | " | 50 | II-2 300 | — | 676 | 0.04 | 661 | 0.05 |
| 10 | " | 50 | — | III-3 180 | 138 | 0.05 | 132 | 0.05 |
| 11 | " | 50 | II-2 150 | III-3 180 | 891 | 0.04 | 891 | 0.04 |
| 12 | " | 50 | II-2 300 | III-3 180 | 933 | 0.04 | 933 | 0.04 |

From the results shown in Table 3 above, it can be seen that the combination of this invention provide a high sensitivity as well as less reduction of sensitivity and less increase of fog when the photographic material including the combination is stored under a high-temperature and high-humidity conditions.

EXAMPLE 4

A silver chloroiodo-bromide emulsion (grain size of 0.25 micron, 19.9 mole % Brm and 0.1 mole % I) was subjected to a gold sensitization and sulfur sensitization. At the preparation of the silver halide grains, $5 \times 10^{-7}$ mole/mole-silver of rhodium was added to the emulsion system. To 1 kg of the silver halide emulsion was added 180 mg of 4-hydroxy-6-methyl-1,3,3a,7-tetraazaindene as a stabilizer. Furthermore, after adding thereto the sensitizing dye of general formula (I) and the compound of general formula (II) as shown in Table 4 below and then adding 200 mg of the compound (III-6), the mixture was maintained at 40° C. and then 450 mg of the polyalkylene oxide compound (IV-21) and 1.2 g of sodium dodecylbenzenesulfonate were added to the emulsion followed by stirring. After one hour and then 15 hours, a hardening agent was added to the mixture. Then, after adding thereto 15 g of the polymer latex described in Japanese Patent Publication No. 5331/'70 per 500 g of the emulsion, the resultant mixture was coated on a polyethylene terephthalate film at a silver coverage of 4.0 g/m².

Each of the samples thus prepared was closely brought into contact with a negative grey contact screen (150 lines/inch, made by Dainippon Screen Mfg. Co. Ltd.) and was exposed through a stop wedge with a step difference of 0.1 (log E) using a semiconductor laser (TP:ML-4001, made by Mitsubishi Electric Corporation) by a manner described in Japanese Patent Publication (Unexamined) No. 151,933/'82.

After exposure, each sample was developed by an automatic processor using a lithographic developer having the following composition for 100 seconds at 27° C. The sensitivity was determined by the reciprocal of the amount of exposure necessary for giving dot of 50%.

Developer Composition:
 Hydroquinone: 15 g
 Addition Product of Formaldehyde and Sodium Hydrogensulfite: 50 g
 Potassium Carbonate: 30 g
 Sodium Sulfite: 2.5 g
 Potassium Bromide: 2.0 g
 Boric Acid: 5.0 g
 Sodium Hydroxide: 3.0 g
 Triethylene Glycol: 40 g
 EDTA.2Na: 1.0 g
 Water to make: 1 liter

TABLE 4

| No. | Sensitizing Dye of Formula (I) | Amount Used ($\times 10^{-6}$ mol/ kg-emulsion) | Compound of Formula (II) | Amount Used (mg/kg-emulsion) | Emulsion Solution Stored For 1 Hour | | Emulsion Solution Stored For 15 Hours | |
|---|---|---|---|---|---|---|---|---|
| | | | | | Relative Sensitivity | Fog | Relative Sensitivity | Fog |
| 1 | I-2 | 40 | — | | 100 (standard) | 0.05 | 56 | 0.07 |
| 2 | | 80 | — | | 81 | 0.05 | 51 | 0.07 |
| 3 | " | 40 | II-2 | 180 | 661 | 0.05 | 641 | 0.05 |
| 4 | | 80 | | 180 | 708 | 0.05 | 692 | 0.05 |
| 5 | I-5 | 40 | — | | 100 (standard) | 0.05 | 52 | 0.07 |
| 6 | | 80 | — | | 78 | 0.05 | 49 | 0.07 |
| 7 | " | 40 | II-3 | 180 | 724 | 0.04 | 708 | 0.04 |
| 8 | | 80 | | 180 | 759 | 0.05 | 741 | 0.05 |
| 9 | I-10 | 40 | — | | 100 (standard) | 0.05 | 51 | 0.07 |
| 10 | | 80 | — | | 85 | 0.05 | 48 | 0.07 |
| 11 | " | 40 | II-4 | 180 | 708 | 0.04 | 692 | 0.04 |
| 12 | | 80 | | 180 | 741 | 0.05 | 724 | 0.05 |

From the results shown in Table 4 above, it can be seen that the combinations of this invention give less desensitization and increase of fog upon storage of the silver halide emulsions in the solution state before coating as compared to the comparison examples using the dyes alone.

While the invention has been described in detail and with reference to specific embodiment thereof, it will be apparent to one skilled in the art that various changes and modifications can be made therein without departing from the spirit and scope thereof.

What is claimed is:

1. A silver halide photographic material comprising a support having thereon at least one silver halide photographic emulsion containing at least one infrared sensitizing dye represented by following general formula (I):

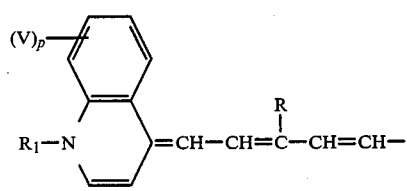

-continued

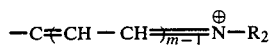

$(X^{\ominus})_{n-1}$ wherein $R_1$ and $R_2$, which may be the same or different, each represents an alkyl group or a substituted alkyl group; R represents a hydrogen atom, a lower alkyl group, a phenyl group, or a benzyl group; V represents a hydrogen atom, a lower alkyl group, an alkoxy group, a halogen atom, or a substituted alkyl group; Z represents a non-metallic atomic group necessary to form a 5-membered or 6-membered nitrogen-containing heterocyclic ring selected from the group consisting of a thiazole nucleus, a benzothiazole nucleus, a naphthothiazole nucleus, a selenazole nucleus, a benzoselenazole nucleus, a naphthoselenazole nucleus, an oxazole nucleus, a benzoxazole nucleus, a naphthaxazole nucleus, a quinoline nucleus, a 3,3-dialkylindolenine nucleus, an imidazole nucleus, a benzimidazole nucleus, a naphthoimidazole nucleus and a pyridine nucleus; X represents an acid anion; and m, n and p each represents 1 or 2; at least one compound represented by the following general formula (II):

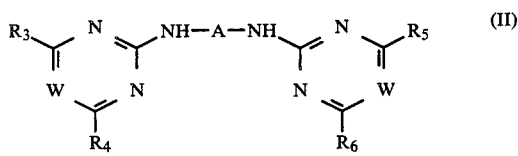

wherein A represents a divalent aromatic residue; $R_3$, $R_4$, $R_5$ and $R_6$, which can be the same or different, each represents a hydrogen atom, a hydroxy group, an alkyl group, an alkoxy group, an aryloxy group, a halogen atom, a heterocyclic nucleus, a heterocyclicthio group, an arylthio group, an amino group, a substituted or unsubstituted alkylamino group, a substituted or unsubstituted arylamino group, a substituted or unsubstituted aralkylamino group, an aryl group, or a mercapto group; at least one of said A, $R_3$, $R_4$, $R_5$ and $R_6$ having at least one sulfo group; and W represents —CH= or —N=; and at least one compound represented by following general formula (III):

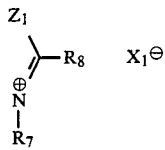
(III)

wherein $Z_1$ represents a non-metallic atomic group necessary to form a 5-membered or 6-membered nitrogen-containing heterocyclic ring selected from the group consisting of a thiazole nucleus, a benzothiazole nucleus, a naphthothiazole nucleus, a selenazole nucleus, a benzoselenazole nucleus, a naphthoselenazole nucleus, an oxazole nucleus, a benzoxazole nucleus, a naphthoxazole nucleus, an imidazole nucleus and a benzimidazole nucleus, $R_7$ represents a hydrogen atom, an alkyl group or an alkenyl group; $R_8$ represents a hydrogen atom, or a lower alkyl group, and $X_1$ represents an acid anion, wherein the at least one compound of general formula (III) is present in a sensitizing amount within the range of form about 0.01 g to about 5 g per mole of silver halide in the at least one silver halide photographic emulsion.

2. The silver halide photographic material as claimed in claim 1, wherein Z in general formula (I) is a thiazole nucleus, a selenazole nucleus, or an oxazole nucleus.

3. The silver halide photographic material as claimed in claim 1, wherein Z in general formula (I) is a benzothiazole nucleus, a naphthothiazole nucleus, a benzoselenazole nucleus, a naphthoselenazole nucleus, or a naphthoxazole nucleus.

4. The silver halide photographic material as claimed in claim 1, wherein W in general formula (II) is —CH=.

5. The silver halide photographic material as claimed in claim 1, wherein $Z_1$ in general formula (III) is a benzothiazole or naphthothiazole nucleus.

6. The silver halide photographic material as claimed in claim 1, wherein $R_1$ and $R_2$ in general formula (I) are an alkyl group, an alkyl group having a sulfo group, or an alkyl group having a carboxy group.

7. The silver halide photographic material as claimed in claim 1, wherein R in general formula (I) is a lower alkyl group or a benzyl group.

8. The silver halide photographic material as claimed in claim 1, wherein the silver halide is silver chlorobromide or silver chloroiodide.

* * * * *